US009474672B2

(12) United States Patent
Robran et al.

(10) Patent No.: US 9,474,672 B2
(45) Date of Patent: Oct. 25, 2016

(54) DEVICE AND METHOD FOR PELVIC ELEVATION AND STABILIZATION OF SURGICAL PATIENT

(71) Applicant: BONE FOAM INC, Plymouth, MN (US)

(72) Inventors: Chad L. Robran, Plymouth, MN (US); Douglas Parsell, Ridgeland, MS (US)

(73) Assignee: Bone Foam Inc., Plymouth, MN (US)

( * ) Notice: Subject to any disclaimer, the term of this patent is extended or adjusted under 35 U.S.C. 154(b) by 360 days.

(21) Appl. No.: 13/736,742

(22) Filed: Jan. 8, 2013

(65) Prior Publication Data

US 2014/0190488 A1 Jul. 10, 2014

(51) Int. Cl.
*A61G 15/00* (2006.01)
*A61G 99/00* (2006.01)
*A61G 13/12* (2006.01)
*A61F 5/01* (2006.01)
*A61B 6/04* (2006.01)

(52) U.S. Cl.
CPC ............... *A61G 99/00* (2013.01); *A61F 5/01* (2013.01); *A61G 13/123* (2013.01); *A61B 6/0421* (2013.01); *A61B 6/0442* (2013.01)

(58) Field of Classification Search
CPC .... A61G 7/00; A61G 7/057; A61G 7/05707; A61G 7/05723; A61G 7/056; A61G 7/07; A61G 13/00; A61G 13/12; A61G 13/1205; A61G 13/123; A61G 13/126
USPC ............. 128/846, 869, 870; 5/600–603, 613, 5/621, 624, 632, 633, 635, 648, 655.9, 5/507.1
See application file for complete search history.

(56) References Cited

U.S. PATENT DOCUMENTS

| | | | |
|---|---|---|---|
| 3,266,061 A * | 8/1966 | Fuechsel | A47C 1/143 5/600 |
| 3,762,404 A | 10/1973 | Sakita | |
| 3,813,091 A * | 5/1974 | Metzger | A61G 7/065 5/114 |
| 3,873,081 A | 3/1975 | Smith | |
| 4,136,858 A | 1/1979 | Petersen | |
| 4,194,601 A | 3/1980 | Yellin | |
| 4,206,524 A * | 6/1980 | Cook | A61G 7/057 5/630 |
| 4,218,792 A | 8/1980 | Kogan | |
| 4,481,943 A | 11/1984 | Michelson | |
| 4,571,761 A * | 2/1986 | Perlin | A47C 15/008 128/845 |
| 4,620,698 A | 11/1986 | Reed | |
| 4,665,573 A * | 5/1987 | Fiore | A47C 27/148 5/731 |
| 4,681,309 A | 7/1987 | Lechner | |
| 4,742,981 A | 5/1988 | Converse | |
| 4,745,647 A | 5/1988 | Goodwin | |
| 4,836,523 A | 6/1989 | Englander | |
| 4,863,788 A | 9/1989 | Bellairs | |
| 5,014,375 A | 5/1991 | Coonrad | |
| 5,016,268 A | 5/1991 | Lotman | |
| 5,018,790 A * | 5/1991 | Jay | A47C 7/021 297/284.1 |

(Continued)

*Primary Examiner* — Michael Brown
(74) *Attorney, Agent, or Firm* — Workman Nydegger (57) ABSTRACT

Devices and methods for supporting and elevating the pelvis of a patient in a supine position during surgery are disclosed. The device comprises a generally flat main body configured to extend from the patient's lower back to the patient's upper legs, a proximal upper surface with a downward slope towards the proximal end, a distal upper surface with a downward slope towards the distal end, and vertically extending ridges on an upper surface of the device for partially containing one or more portions of the patient's body. In use, the device is positioned on a surgical platform beneath the iliosacral region of the patient.

20 Claims, 5 Drawing Sheets

(56) References Cited

U.S. PATENT DOCUMENTS

| | | | |
|---|---|---|---|
| 5,125,123 A | 6/1992 | Engle | |
| 5,289,828 A | 3/1994 | Toth | |
| 5,369,825 A | 12/1994 | Reesby | |
| 5,462,551 A | 10/1995 | Bailey | |
| 5,479,667 A * | 1/1996 | Nelson | A47C 20/027 |
| | | | 5/632 |
| 5,645,079 A | 7/1997 | Zahiri | |
| 5,754,997 A | 5/1998 | Lüssi | |
| 5,775,334 A | 7/1998 | Lamb | |
| 5,809,597 A | 9/1998 | Shaw | |
| 5,819,743 A | 10/1998 | McMillin | |
| 5,906,205 A | 5/1999 | Hiebert | |
| 6,032,669 A | 3/2000 | Klein | |
| 6,357,066 B1 * | 3/2002 | Pierce | A61B 6/0442 |
| | | | 5/710 |
| 6,371,894 B1 * | 4/2002 | Hill | A63B 21/00047 |
| | | | 128/845 |
| 6,553,995 B1 | 4/2003 | Cole et al. | |
| 6,745,774 B2 * | 6/2004 | Fessler | 128/845 |
| 6,810,543 B2 * | 11/2004 | Fuhriman | 5/632 |
| D579,706 S * | 11/2008 | Cox | D6/601 |
| 7,694,369 B2 * | 4/2010 | Hinders | A61G 13/12 |
| | | | 5/613 |
| D670,941 S * | 11/2012 | Vernon | D6/716.4 |
| 8,469,911 B2 * | 6/2013 | Hiebert | A61F 5/3769 |
| | | | 128/845 |
| 2012/0259370 A1 * | 10/2012 | Vaidya | 606/281 |

* cited by examiner

DEVICE AND METHOD FOR PELVIC ELEVATION AND STABILIZATION OF SURGICAL PATIENT

BACKGROUND OF THE INVENTION

1. The Field of the Invention

The present invention relates to devices and methods for elevating the pelvic position of a surgical patient in a supine position.

2. Background and Relevant Art

Percutaneous bone fixation is a technique used by orthopedic surgeons for the stabilization of unstable fractures. It involves the manipulation, with X-ray guidance, of the fracture into an acceptable position, and the insertion of metal pins through the skin into one bone fragment and across the fracture line into an adjacent bone fragment. Percutaneous fixation falls into the category of minimally invasive surgery, which has become very popular and well described for pelvic and acetabular fractures.

Surgeons commonly perform percutaneous fixation on a radiolucent operating table. A patient undergoing the procedure usually lies in a supine position, i.e. with the front (anterior) facing up and the back (posterior) facing down. Because the operating tables are generally covered with a mattress, the patient tends to "sink" into the mattress a couple of inches. During operation, the patient should be centered on the table; however, the table is generally wider than most all patients. They are designed for the largest patients. As a result, when a patient is centered on the table, the pelvic bone is usually far from the table's edge and in the aforementioned sunken position relative to the plane of the mattress surface.

In many percutaneous fixation procedures, a surgeon must be able to insert drills, pins, screws, or other equipment with a posterior-to-anterior vector. The orientation of the patient, however, can cause the surgeon's hands and equipment to compete or "bump into" the table and mattress, thus compromising the surgeon's ability to place implants at the desired posterior to anterior vector. To overcome this problem, surgeons have conveniently placed a raised bump, such as a roll of sterile towels or a blanket, under the sacrum or tailbone of the patient in an attempt to selectively elevate the patient in order to provide better access to posterolateral aspects of the buttock with the appropriately directed drilling and implant placement.

Lifting a patient with such a sacral "pad", however, can cause the patient's body to become unstable as the patient tends to rock right and left as if to fall off the pad. Typical sacral pads are conventionally made using sheets, blankets, or towels that are folded, stacked, and often taped so they do not fall apart. This method, however, creates instability of the patient, inconsistency of surface, and, at times, creates interference if done improperly. Furthermore, the shapes of such sacral pads are not optimized to evenly distribute the patient's weight, and the hardness of the pads does not always provide appropriate cushioning to the patient's body. As a result, makeshift sacral pads tend to increase point pressures via body weight loading of bony protuberances, which may aggravate soft tissue damage and breakdown.

BRIEF SUMMARY

Recognizing problems associated with conventional sacral pads, the inventors have discovered solutions which overcome one or more of the foregoing or other problems in the art, which solutions involve methods and apparatus configured to allow the convenient positioning of a surgical patient in the supine position in a stable and comfortable manner. One or more implementations of the invention provide an iliosacral cradle that elevates the ilium and the sacrum, yet provide stable support to the buttock and flank. The iliosacral cradle is configured to allow for access to the anatomy, e.g., posterolateral buttock, for proper positioning of drills, implants, and other surgical equipment to achieve fracture reduction or fixation. The iliosacral cradle elevates the patient's pelvis above the surgical table surface adequately to allow a surgeon to position his/her hands, while holding surgical tools, for the desired posterior-to-anterior vector placement. The cradle distributes the patient's weight over the upper-legs, buttocks, and lower-back of the patient and provides adequate cushioning to hard and soft tissues under pressure. As a result, the cradle provides stable weight support and reduces pressure on body tissue.

One aspect of the invention relates to a device for supporting and elevating the pelvis of the patient in the supine position during surgery. One or more implementations of the invention provide an iliosacral cradle comprising a generally flat main body and at least two vertically extending lateral ridges on an upper surface of the main body. According to one embodiment, the main body of the cradle is configured to extend from the patient's lower back to the patient's upper legs when the main cradle body is positioned under the posterior iliosacral region of the patient. The main body of the cradle has a proximal end section configured to be positioned beneath the patient's lower back, a distal end section configured to be positioned beneath the patient's upper legs, and a medial section configured to be positioned beneath the patient's buttocks. In a preferred embodiment, the medial section of the main cradle body can be narrower (i.e., have a smaller width) than the proximal end and distal end sections. On the one hand, this shape provides reliable, stable support to the lumbar and legs of the patient. On the other hand, the cradle design provides convenient access to the posterior aspect of the patient's buttock areas.

In one or more implementations of the invention, the proximal end section of the cradle can have a proximal upper surface portion with a downward sloping decline towards the proximal end so that there is an appropriate skin pressure transition. Similarly, the distal end section of the cradle can have a distal upper surface portion with a downward slope decline towards the distal end. In addition, the medial section of the cradle can have a medial upper surface portion that is substantially level without incline or decline.

In one or more implementations of the present invention, the cradle may further comprise two distal-lateral ridges extending vertically along or near the distal-lateral edges of the distal upper surface, and two proximal-lateral ridges extending vertically along or near the proximal-lateral edges of the proximal upper surface. In one or more implementations, the cradle may also comprise a vertically extending ridge along a mid-line of the major axis of the device, which can be positioned adjacent to the downward sloping decline of the distal upper surface.

This summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. Additional features and advantages of the invention will be set forth in the description which follows, and in part will be obvious from the description and appended claims, or may be learned by the practice of the invention. The features and advantages of the invention may be realized and obtained by means of the instruments and combinations particularly pointed out in the appended claims.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the figures are not necessarily drawn to scale, and that elements of similar structure or function are generally represented by like reference numerals for illustrative purposes throughout the figures. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Implementations of the present invention involve methods and apparatus configured to allow the convenient, reliable and secure positioning of a surgical patient. In one aspect, the invention provides an iliosacral cradle that elevates the ilium and the sacrum, while yet providing stable support to the buttock and flank. The iliosacral cradle is configured to allow for access to the anatomy, e.g., posterolateral buttock for proper positioning of drills, implants, and other surgical equipment to achieve fracture reduction or fixation. The iliosacral cradle elevates the patient's pelvis above the surgical table surface adequately to allow a surgeon to position his/her hands, while holding surgical tools, for the desired posterior-to-anterior vector placement. The cradle distributes the patient's weight over the upper-legs, buttocks, and lower-back of the patient and provides adequate cushioning to hard and soft tissues under pressure. As a result, the cradle provides stable weight support and reduces pressure on body tissue.

One or more implementations of the present invention provide a body support apparatus, or an iliosacral cradle, made of medium density, open cell foam support. In one embodiment, the cradle is prefabricated and pre-contoured to conform to the general shape of a patient's body. When the cradle is placed under the patient, the contour of the cradle transitions from the bicurved buttock region, to the flat tailbone region, to the pre-molded back and flank area.

One or more implementations of the present invention provides a body support device that elevates the patient's pelvis off the operation table, which is convenient when surgeons wish to surgically apply percutaneous internal fixation with screws for pelvic or acetabular fractures. The body support device can be symmetric to allow for simultaneous bilateral exposure and surgery. It can be shielded from direct physical contact with the surgical field via a sterile drape. This approach is easily achieved due to the device being largely posterior (and lateral at the flank) to the patient.

In one or more implementations, the body support device is soft to avoid generation of significantly increased point pressures via body weight loading of bony protuberances. The contoured shape conforming to the patient's body further optimizes distribution of body weight load. Optimum load distribution has been clinically demonstrated to reduce the occurrence of procedure related soft tissue damage and breakdown.

One or more implementations may be manufactured as a disposable body support device. Alternative implementation may be manufactured as a reusable product. The reusable version may advantageously be coated with a flexible, fluid-impermeable polymer coating to allow for cleansing and sterilization and increase the overall durability of the device.

One or more implementations of the invention can be radiolucent to allow for proper X-ray imaging. Suitable materials for fabricating the device include, but are not limited to, polystyrene, acrylonitrile, styrene acrylonitrile, polyvinyl chloride (PVC), polyethylene terephthalate (PET), polysulfone, polyethylene, polypropylene, high density and low density polyethylene materials, nylon materials, polyamides, oxygen barrier materials such as PET, PPOH, PVDC (polyvinyl dichloride), polytetrafluoroethylene (PTFE), polyvinylidene chloride, polypropylene, poly-butylene, polyisobutylene, and the like. Also to be contemplated as plastic materials would be elastomerics, such as rubber materials or synthetic rubber materials, styrene butadiene, isopropylene, and the like. One skilled in the art will appreciate that other natural and synthetic supportive materials may be used so long as they meet the design criteria described herein. The various parts of the device may be produced by molding, extrusion, cutting, and/or adhesion, as well as other techniques known in the art.

Figure 1:
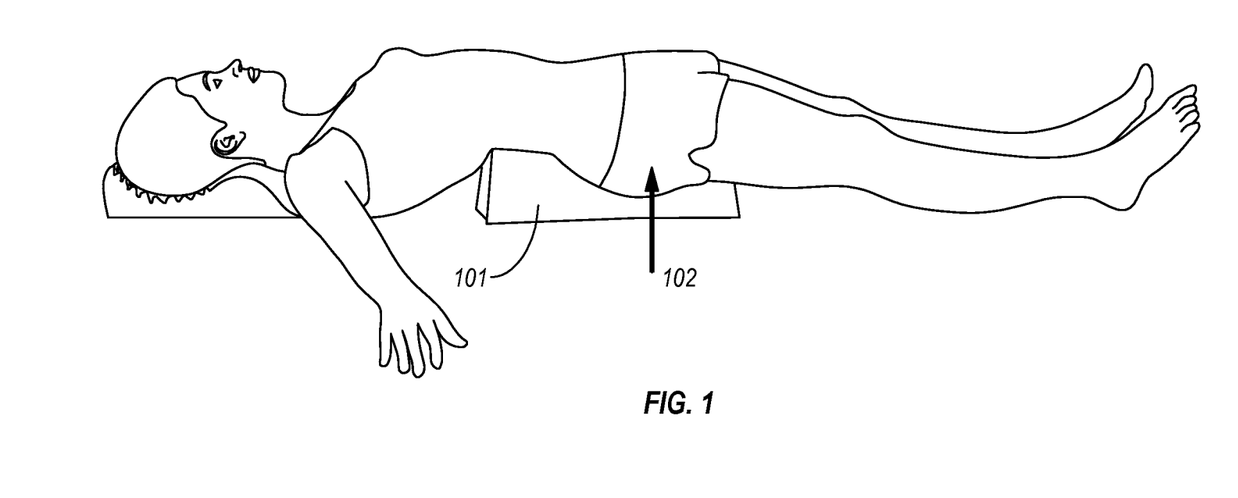
FIG. 1 is a patient laying in the supine position on an iliosacral cradle according to an embodiment of the invention, with the cradle positioned under the lower back, buttocks, and upper legs and selectively elevating the pelvic area so as to expose the posterolateral portions of the buttocks for surgical operation.

Referring now the Figures, FIG. 1 illustrates the typical surgical utilization of an iliosacral supporting device. The device 101 under the patient denotes an embodiment of the iliosacral cradle properly positioned beneath the lumbar region of the patient's body. FIG. 1 illustrates the general scale and size of the disclosed device. The included arrow 102 indicates a posterior-anterior vector for surgical insertion of orthopedic hardware for stabilization of pelvic fractures. The elevation of the patient's pelvis, provided by the disclosed device, allows the surgeon to adequately lower his/her hand position, thus allowing for availability of an optimum hardware insertion path.

FIGS. 2-7 illustrate the various views of an implementation of the invention as an iliosacral cradle 200. The cradle 200 as implemented in the example shown in FIGS. 2-7 has a generally flat main body 202. The main body 202 of the cradle 200 is configured to extend from the patient's lower back to the patient's upper legs when the main body is positioned under the posterior iliosacral region of the patient. The main body 202 of the cradle 200 has a proximal end section near the proximal end 214 configured to be positioned beneath and to support the patient's lower back. The main body 202 also has a distal end section near the distal end 216 configured to be positioned beneath and to support the patient's upper legs. The main body 202 further comprises a medial section 218 approximately mid-way between the proximal end 214 and distal end 216, which is configured to be positioned beneath and to support the patient's buttocks. The medial section 218 can have an upper surface that is substantially level, without decline or incline. Alternatively, medial section 218 can have a desired incline and/or decline as desired.

Figure 4:
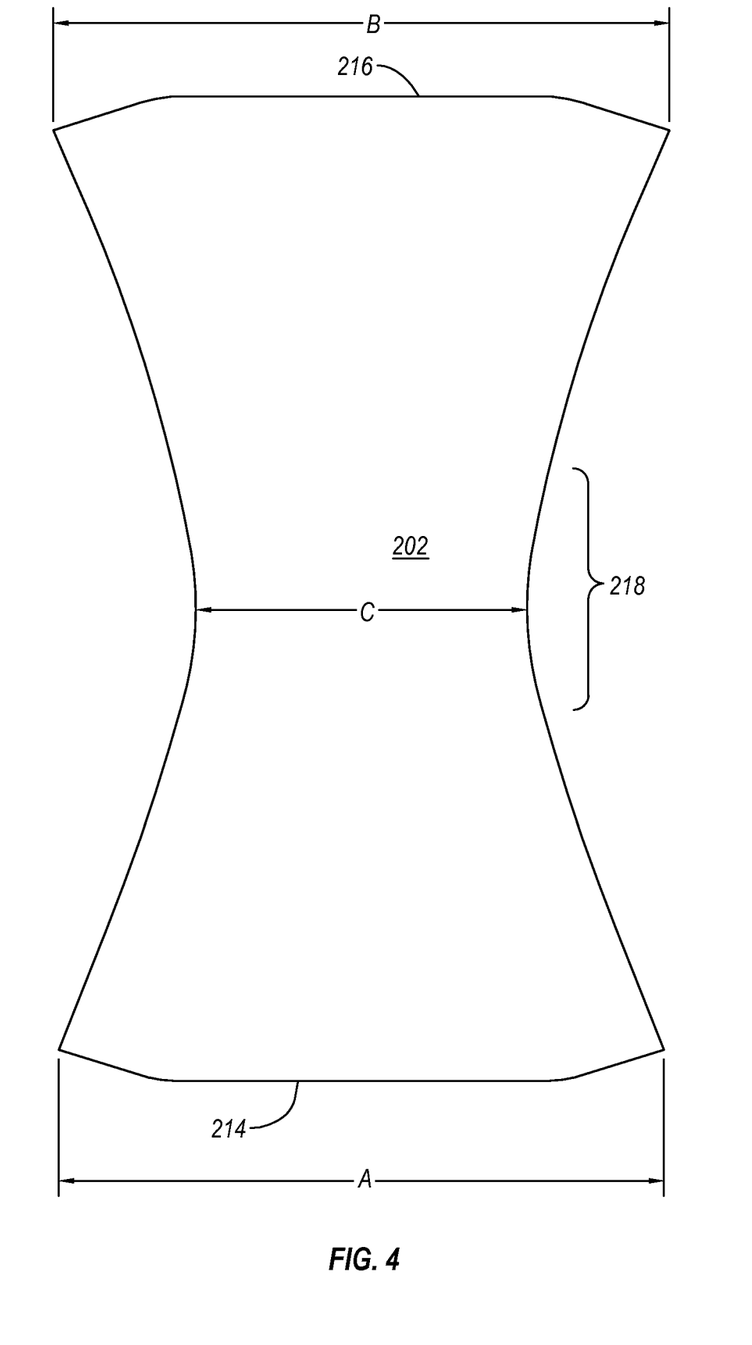
FIG. 4 is a bottom plan view of the iliosacral cradle of FIG. 2.

In a preferred implementation of the cradle 200 as shown in FIG. 4, a narrowest portion of the medial section 218 of the main body 202 has a smaller cross-wise width, as indicated by arrows C, than a maximum cross-wise width of the proximal end section near proximal end 214 as indicated by arrows A. Similarly, the narrowest cross-wise width of the medial section 218 of the main body 202 can also be smaller than the maximum cross-wise width of the distal end section near proximal end 216 as indicated by arrows B. The changes in width can be provided by a generally curved side surface and/or two or more straight surfaces joined together. On the one hand, the wider proximal and distal end sections provide increased stability and wider support to the lumbar and legs of the patient. On the other hand, the narrower medial section 218 provides increased and convenient access to the posterior aspect of the patient's buttock areas.

Figure 2:
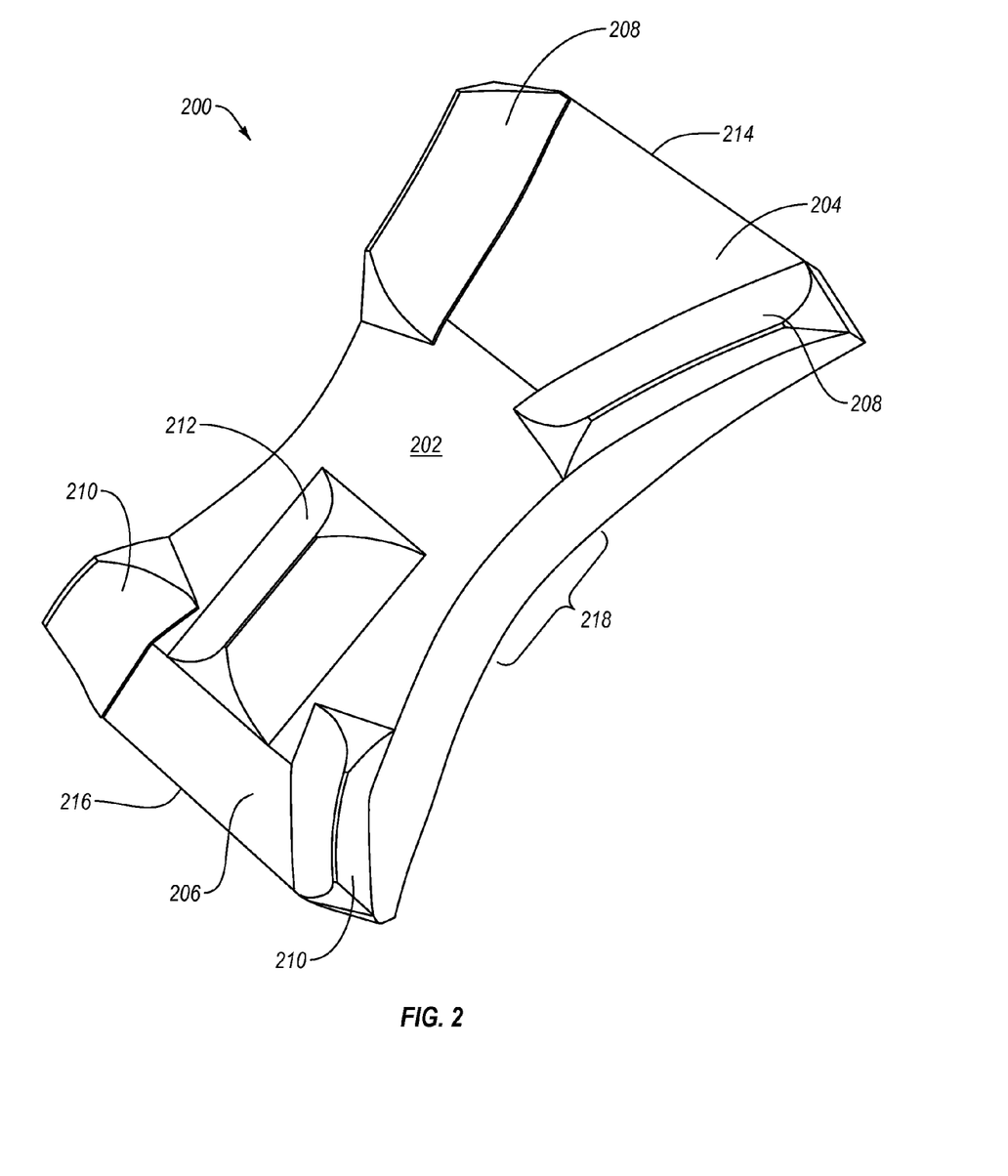
FIG. 2 is a top, right, front perspective view illustrating an example of an iliosacral cradle according to one embodiment of the invention.

As illustrated in FIG. 2, the proximal end section of the cradle has a proximal upper surface 204 with a downward slope or decline towards the proximal end 214. Similarly, the distal end section of the cradle 200 has a distal upper surface 206 with a downward slope or decline towards the distal end 216. One skilled in the art can adjust the extent and degree of the slope of the proximal and distal upper surfaces to create optimal comfort and support when the device is positioned under the patient's pelvic area.

In one or more implementations of the present invention, such as the implementation exemplified in FIGS. 2-7, the cradle 200 comprises two distal-lateral ridges 210 extending vertically along or near the distal-lateral edges of the distal upper surface 206, and two proximal-lateral ridges 208 extending vertically along or near the proximal-lateral edges of the proximal upper surface 204. In this implementation, the cradle 200 also comprises a vertically extending, distal-central ridge 212 along a mid-line of a major axis of the device adjacent to the distal upper surface 206. The foregoing ridges provide lateral support to improve stability of the patient. They can also help to more evenly distribute the patient's body weight.

In one or more embodiments of the invention, the device is contoured to fit the upper legs, bicurved buttocks, flat tailbone region, and back and flank of the patient. For instance, as in the device 200 shown in FIG. 2, the distal-central ridge 212 and the main body 202 form two concave trough contours that functionally contain the patient's posterolateral buttock during surgical utilization. The distal-central ridge 212, the distal-lateral ridges 210 and the main body 202 form two concave trough contours that functionally contain the patient's upper legs during surgical utilization. The proximal-lateral ridges 208 and the main body 202 form a concave trough contour that functionally contains the patient's lower back during surgical utilization.

Figure 3:
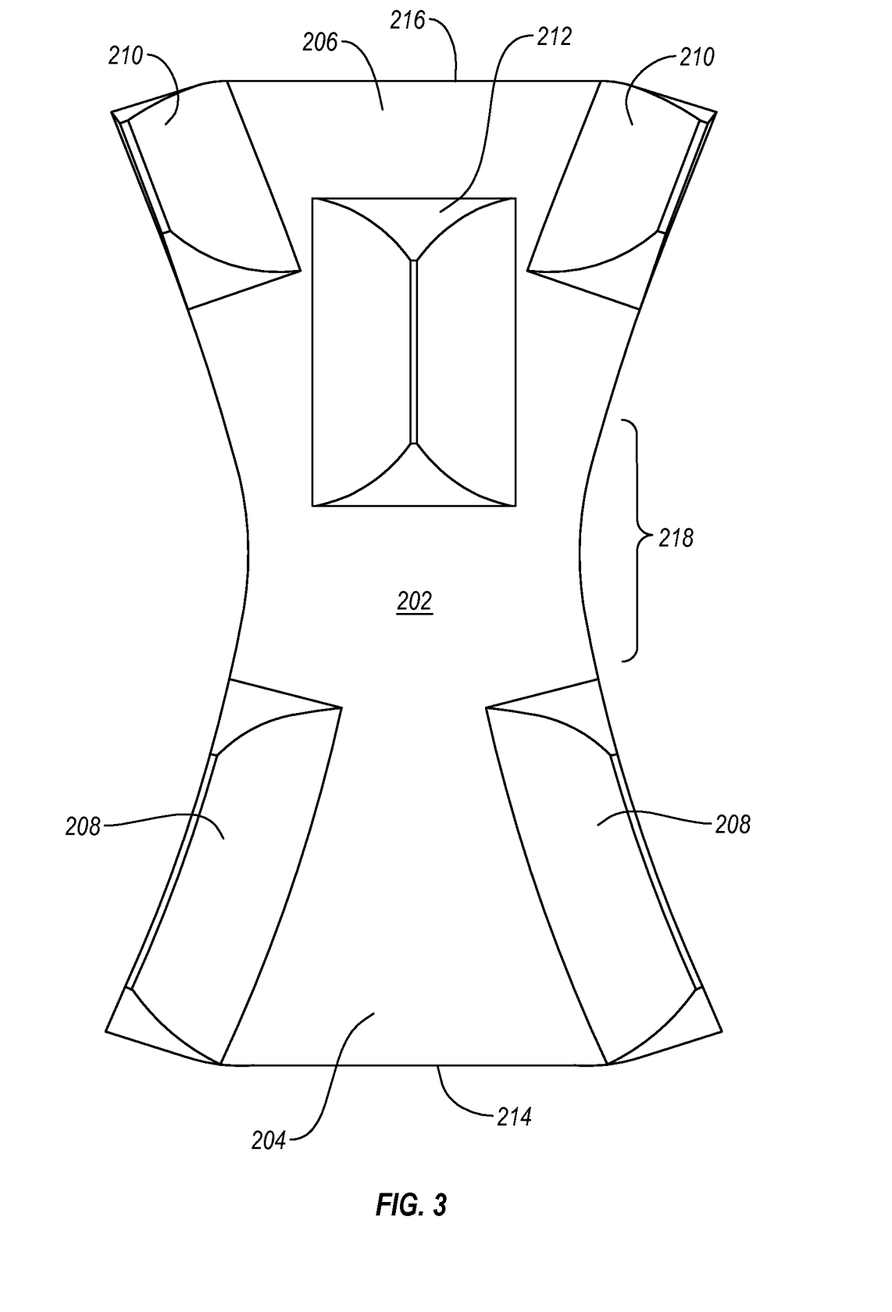
FIG. 3 is a top plan view of the iliosacral cradle of FIG. 2.
Figure 5:
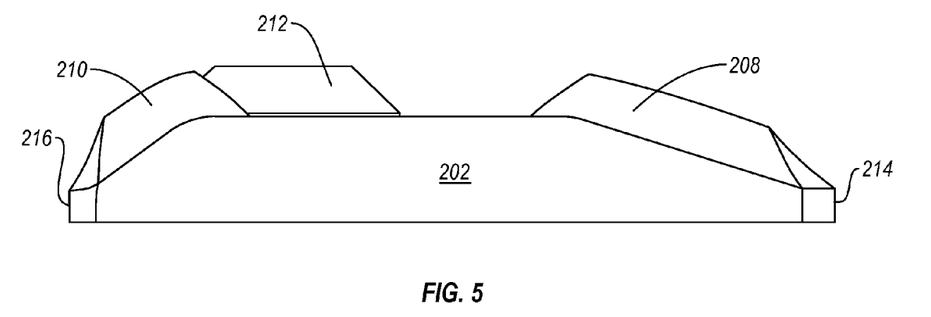
FIG. 5 is a right side elevation view of the iliosacral cradle of FIG. 2.
Figure 6:
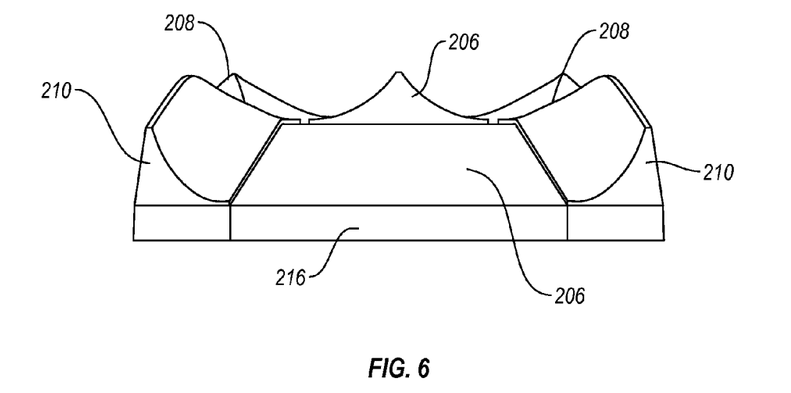
FIG. 6 illustrates a front elevation view of the iliosacral cradle of FIG. 2 showing the distal end of the cradle.
Figure 7:
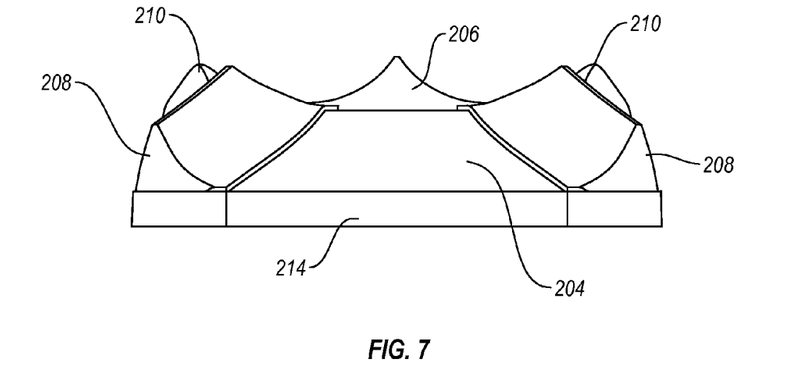
FIG. 7 illustrates a back elevation view of the iliosacral cradle of FIG. 2 showing the proximal end of the cradle.

In the implementation shown in the Figures, the proximal-lateral ridges 208 can be longer than the distal-lateral ridges 210 as illustrated in FIGS. 2, 3, and 5. Meanwhile, the proximal-lateral ridges 208 can have a smaller inter-ridge distance than the distal-lateral ridges 210 as illustrated in FIGS. 6 and 7. The different inter-ridge distances correspond to the generally narrower lower back region and the wider upper thigh region of a typical patient. One skilled in the discipline would appreciate that the length of the ridges and the inter-ridge distance can be adjusted according to different sizes of cradles and/or patients.

Although softness is desirable to improve cushioning, the materials for the device should be firm enough to provide adequate support for the patient for a minimal elevation. In one or more embodiments of the invention, the device is firm enough to maintain a minimum patient elevation of one inch. This objective of the device usually requires the thickness of the medial section 218 of the cradle to be more than one and one quarters of an inch thick to account for compression by the patient during use. The thickness as height of the main body in the medial region can be 1.0 to 12 inches, preferably 1.5 to 7 inches, more preferable 2.5 to 6 inches.

In one or more implementations, an auxillary foam pad may be provided in addition to the contoured pad described herein. The axillary pad (not shown) may be constructed of a foam density similar to the main body 202 of the iliosacral cradle 200, which may be positioned directly beneath the main body 202 of the device 200 during surgical utilization. The auxillary pad can be rectangular or contoured similar to pad 200. A function of the auxillary foam pad is to provide the surgeon with the ability to increase the functional vertical height of the iliosacral support device on a case-by-case basis. Multiple auxillary foam pads can provide even greater versatility.

Another aspect of the invention relates to methods for elevating a patient's pelvis during a surgical procedure using an iliosacral cradle. In one or more embodiments of the invention, the method comprises: (1) providing a surgical platform; (2) placing an iliosacral cradle on an upper surface of the surgical platform; and (3) positioning the device underneath the iliosacral region of the patient, thereby elevating the pelvis of the patient.

In one or more embodiments of the present invention, the method further comprises exposing a posterolateral buttock of the patient. In one or more embodiments, the surgical procedures involve treatment of pelvic or acetabular fractures. Some of the methods involve surgical procedure for percutaneous internal fixation with screws for pelvic or acetabular fractures. In these procedures, the operation platforms are preferably radiolucent operation tables.

As mentioned above, a surgeon may need to change the height of the patient. The surgeon's need for increased vertical height may stem from a unique surgical situation, as dictated by the presenting trauma, from greater device compression generated by atypically great patient body weight, or from personal surgeon preference. Based on this need, an embodiment of the inventive methods further comprises placing an auxillary pad beneath the main body of the device, thereby further elevating the pelvis of the patient. One or more auxillary pads can be used as needed or desired.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A device for supporting and elevating the pelvis of a patient in a supine position for surgery, comprising:
   a generally flat main body configured to be placed on an upper surface of a surgical platform to support and elevate the pelvis of the patient during a surgical procedure, the main body comprising:
      a proximal end section having a proximal upper surface configured to be positioned beneath and support the patient's lower back,
      a distal end section having a distal upper surface configured to be positioned beneath and support the patient's upper legs, and
      a medial section having a medial upper surface configured to be positioned beneath and support the patient's buttocks, the medial section having a smaller cross-wise width than cross-wise widths of the proximal end and distal end sections in order to provide access to a posterolateral aspect of the patient's buttocks during a surgical procedure; and
   a distal-central ridge extending vertically from an upper surface of the main body along a mid-line of a major axis of the main body, the distal-central ridge and the main body forming two concave trough contours, a first concave trough contour on one side of the distal-central ridge supporting a first posterolateral buttock and a second concave trough contour on an opposite side of the distal-central ridge supporting a second posterolateral buttock during a surgical procedure.

2. A device as in claim 1, wherein
   at least a portion of the proximal upper surface has a downward slope declining towards a proximal end; and
   at least a portion of the distal upper surface has a downward slope declining towards a distal end.

3. A device as in claim 1, further comprising two spaced-apart distal-lateral ridges extending along or near lateral edges of the distal upper surface that form a concave trough contour that contains the patient's upper legs during a surgical procedure.

4. A device as in claim 1, further comprising two spaced-apart proximal-lateral ridges extending along or near lateral edges of the proximal upper surface that form a concave trough contour that contains the patient's lower back during a surgical procedure.

5. A device as in claim 1, further comprising two spaced-apart distal-lateral ridges extending along or near lateral edges of the distal upper surface that form a concave trough contour that contains the patient's upper legs during a surgical procedure and two spaced-apart proximal-lateral ridges extending along or near lateral edges of the proximal upper surface that form a concave trough contour that contains the patient's lower back during a surgical procedure.

6. A device as in claim 1, wherein the main body comprises open cell polymer foam.

7. A device as in claim 6, wherein the polymer foam is coated with a flexible, fluid-impermeable polymer coating.

8. A device as in claim 1, wherein the device comprises radiolucent material.

9. A device as in claim 1, wherein the main body has a height and/or flexibility, coupled with sufficient firmness, so as to maintain a minimum elevation of the patient's pelvis of one inch, from the upper surface of the surgical platform, during use.

10. A device as in claim 9, wherein the main body has a firmness with sufficient yield to reduce pressure at and provide a comfortable support for high-pressure, soft-tissue areas.

11. A device as in claim 1, wherein the main body is contoured to approximately fit against the upper legs, bicurved buttocks, flat tailbone region, and back and flank of a patient.

12. A device as in claim 1, further comprising an auxiliary pad configured to be positioned directly beneath the main body to further elevate a patient's pelvis during use.

13. A method for elevating a patient's pelvis during a surgical procedure, comprising:
    providing a surgical platform;
    placing a device for supporting and elevating the pelvis of a patient in a supine position on an upper surface of the surgical platform, the device comprising
       a generally flat main body configured to be placed on an upper surface of a surgical platform to support and elevate the pelvis of the patient during a surgical procedure, the main body comprising:
          a proximal end section having a proximal upper surface configured to be positioned beneath and support the patient's lower back,
          a distal end section having a distal upper surface configured to be positioned beneath and support the patient's upper legs, and
          a medial section having a medial upper surface configured to be positioned beneath and support the patient's buttocks, the medial section having a smaller cross-wise width than cross-wise widths of the proximal end and distal end sections in order to provide access to a posterolateral aspect of the patient's buttocks during the surgical procedure; and
       a distal-central ridge extending vertically from an upper surface of the main body along a mid-line of a major axis of the main body, the distal-central ridge and the main body forming two concave trough contours, a first concave trough contour on one side of the distal-central ridge supporting a first posterolateral buttock and a second concave trough contour on an opposite side of the distal-central ridge supporting a second posterolateral buttock during the surgical procedure; and
    positioning the device underneath the iliosacral region of the patient, thereby elevating the pelvis of the patient.

14. A method as in claim 13, further comprising exposing the posterolateral buttocks of the patient.

15. A method as in claim 13, wherein the surgical procedure involves treatment of one or more pelvic or acetabular fractures.

16. A method as in claim 15, wherein the surgical procedure provides percutaneous internal fixation with screws for the one or more pelvic or acetabular fractures.

17. A method as in claim 13, wherein the surgical platform comprises a radiolucent surgical table.

18. A method as in claim 13, the method further comprising placing an auxiliary pad above the surgical platform and beneath the main body of the device, thereby further elevating the pelvis of the patient.

19. A device for supporting and elevating the pelvis of a patient in a supine position for surgery, comprising:
    a generally flat main body at least partially formed from a polymer foam and comprising:

a generally flat lower surface configured for placement on an upper surface of a surgical platform to support and elevate the pelvis of the patient, a proximal end section having a proximal upper surface configured to be positioned beneath and support the patient's lower back, a distal end section having a distal upper surface configured to be positioned beneath and support the patient's upper legs, and a medial section having a medial upper surface configured to be positioned beneath and support the patient's buttocks, the medial section having a smaller cross-wise width than cross-wise widths of the proximal end and distal end sections in order to provide access to a posterolateral aspect of the patient's buttocks during a surgical procedure;

two distal-lateral ridges extending vertically from the distal upper surface of the main body and positioned along distal-lateral edges of the distal upper surface that form a concave trough contour that contains the patient's upper legs during a surgical procedure; and two proximal-lateral ridges extending vertically from the proximal upper surface of the main body and positioned along proximal-lateral edges of the proximal upper surface that form a concave trough contour that contains the patient's lower back during a surgical procedure.

20. A device as in claim 19, further comprising a distal-central ridge extending vertically from an upper surface of the main body along a mid-line of a major axis of the main body, the distal-central ridge and the main body forming two concave trough contours for supporting a patient's buttocks during a surgical procedure.

* * * * *

UNITED STATES PATENT AND TRADEMARK OFFICE
CERTIFICATE OF CORRECTION

PATENT NO. : 9,474,672 B2  
APPLICATION NO. : 13/736742  
DATED : October 25, 2016  
INVENTOR(S) : Robran et al.

Page 1 of 1

It is certified that error appears in the above-identified patent and that said Letters Patent is hereby corrected as shown below:

Column 1
Line 29, change "most all patients" to --most patients--

Column 3
Line 18, change "therefor to be considered to be limiting" to --therefor considered to be limiting--

Column 6
Line 11, change "support for the patient for a minimal" to --support to the patient for a minimal--

Signed and Sealed this
Twenty-fourth Day of January, 2017

Michelle K. Lee
*Director of the United States Patent and Trademark Office*